US012558445B2

(12) United States Patent
Tansu et al.

(10) Patent No.: US 12,558,445 B2
(45) Date of Patent: Feb. 24, 2026

(54) SYSTEM FOR IRRADIATING OBJECTS WITH ULTRAVIOLET LIGHT

(71) Applicants: LEHIGH UNIVERSITY, Bethlehem, PA (US); ST LUKE'S UNIVERSITY HOSPITAL, Bethlehem, PA (US)

(72) Inventors: Nelson Tansu, Adelaide (AU); Axel Y. Tansu, Adelaide (AU); Adela Gozali Yose, Adelaide (AU); Renbo Song, Breinigsville, PA (US); Anthony Jeffers, Macungie, PA (US); Grant Reed, Kintnersville, PA (US); Ankhitha Manjunatha, Breinigsville, PA (US); Theodore L. Bowen, Bath, PA (US); Christopher Roscher, Coopersburg, PA (US); Jay W. Johnson, Coopersburg, PA (US); Eric Tesoriero, Nazareth, PA (US)

(73) Assignee: Lehigh Univeristy, Bethlehem, PA (US)

( * ) Notice: Subject to any disclaimer, the term of this patent is extended or adjusted under 35 U.S.C. 154(b) by 678 days.

(21) Appl. No.: 17/996,258

(22) PCT Filed: Apr. 14, 2021

(86) PCT No.: PCT/US2021/027301
§ 371 (c)(1),
(2) Date: Oct. 14, 2022

(87) PCT Pub. No.: WO2021/211720
PCT Pub. Date: Oct. 21, 2021

(65) Prior Publication Data
US 2023/0201389 A1    Jun. 29, 2023

Related U.S. Application Data

(60) Provisional application No. 63/010,354, filed on Apr. 15, 2020.

(51) Int. Cl.
*A61L 2/10* (2006.01)
*A61L 2/26* (2006.01)

(52) U.S. Cl.
CPC .................. *A61L 2/10* (2013.01); *A61L 2/26* (2013.01); *A61L 2202/11* (2013.01);
(Continued)

(58) Field of Classification Search
CPC .......... A61L 2/10; A61L 2/26; A61L 2202/11; A61L 2202/122; A61L 2202/24; A61L 2202/26
See application file for complete search history.

(56) References Cited

U.S. PATENT DOCUMENTS 9,662,411 B2    5/2017  Rizzone
11,439,717 B1 *  9/2022  Eggleston ................. A61L 2/10
(Continued)

FOREIGN PATENT DOCUMENTS

CN        2412575      1/2001
CN       109371635     2/2019
(Continued)

*Primary Examiner* — Jennifer Wecker
*Assistant Examiner* — Brady C Pillsbury
(74) *Attorney, Agent, or Firm* — Christopher R. Powers; Endress+Hauser (USA) Holding, Inc.

(57) ABSTRACT

A system for ultraviolet irradiation of objects and a method of using this system is disclosed. The system includes: an illuminating device positioned in a center section of an octagon shaped a base area and including one or more elongated light sources, each emitting ultraviolet light given by shortwave ultraviolet light (UV-C light) and extending in parallel to a normal on the base area; a set of rotatable mesh grids arranged around the base area such that the mesh grids surround the illuminating device and configured to be equipped with the objects; and a set of reflectors including a set of movable side reflectors, wherein the reflectors are configured to be arranged such, that they form a resonator (Continued)

surrounding the mesh grids surrounding the illuminating device.

17 Claims, 7 Drawing Sheets

(52) U.S. Cl.
CPC ..... *A61L 2202/122* (2013.01); *A61L 2202/24* (2013.01); *A61L 2202/26* (2013.01)

(56) References Cited

U.S. PATENT DOCUMENTS

| | | | | |
|---|---|---|---|---|
| 2012/0086352 A1 | | 4/2012 | Espiau et al. | |
| 2013/0171037 A1 | * | 7/2013 | Im | A61L 2/10 250/455.11 |
| 2013/0256560 A1 | * | 10/2013 | Yerby | A61L 2/24 250/455.11 |
| 2014/0348701 A1 | * | 11/2014 | Kirschman | A61L 9/20 422/4 |
| 2016/0279275 A1 | | 9/2016 | Deshays et al. | |
| 2017/0000917 A1 | * | 1/2017 | Stibich | A61L 2/20 |
| 2017/0216473 A1 | | 8/2017 | Rizzone | |
| 2021/0299304 A1 | * | 9/2021 | Concannon | A61L 2/26 |

FOREIGN PATENT DOCUMENTS

| | | | |
|---|---|---|---|
| JP | H0488942 A | 3/1992 |
| JP | 2008288542 A | 11/2008 |
| WO | 2014186741 A1 | 11/2014 |

* cited by examiner

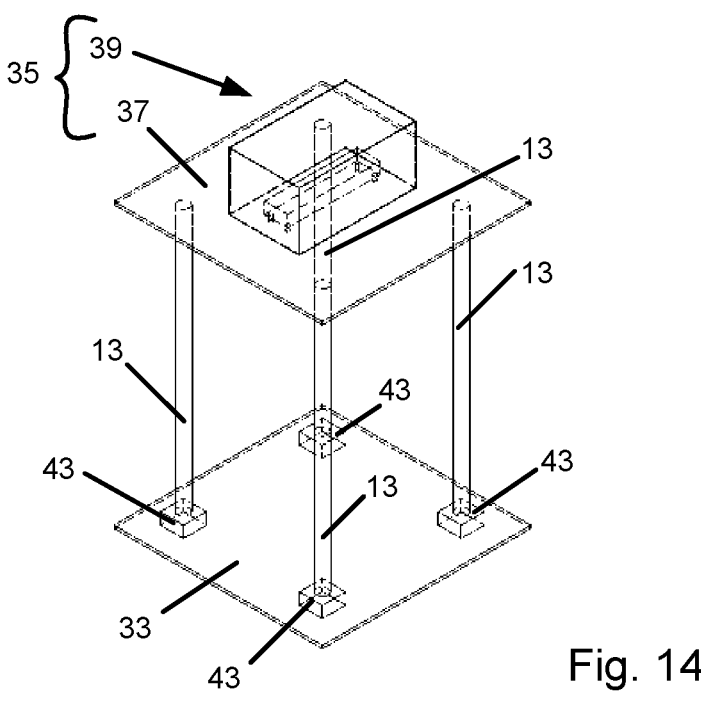
Fig. 14
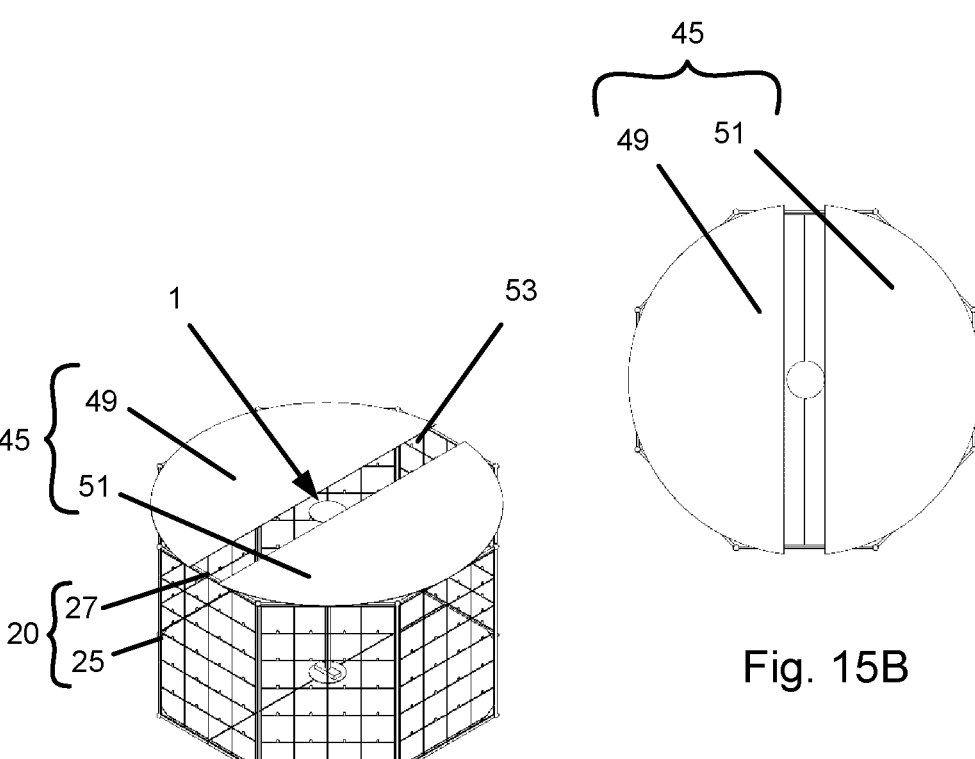
Fig. 15A
Fig. 15B

SYSTEM FOR IRRADIATING OBJECTS WITH ULTRAVIOLET LIGHT

CROSS-REFERENCE TO RELATED APPLICATIONS

The present application is related to and claims the priority benefit of U.S. Provisional Patent Application No. 63/010,354, filed on Apr. 15, 2020, and International Patent Application No. PCT/US2021/027301, filed Apr. 14, 2021, the entire contents of which are incorporated herein by reference.

TECHNICAL FIELD

The present disclosure relates to a system for irradiating objects with short wavelength ultraviolet light and a method of using the system.

BACKGROUND

The coronavirus or Covid-19 disease has caused an unprecedented shortage of personal protective equipment for medical professionals, patients and other people. Specifically, the need for face masks, in particular face masks meeting the classification N95 of air filtration of the U.S. National Institutes for Occupational Safety and Health filtering at least 95% of airborne particles, has driven the need to have the ability to sufficiently disinfect face masks to allow for multiple uses per face mask. Multiple uses could result in a significant increase in the availability of face masks for medical professionals, patients and the community confronted with respiratory-based diseases.

Ultraviolet germicidal irradiation using short wavelength ultraviolet light (e.g., UV-C light) provided by a light source is a method that can be used to disinfect, to decontaminate and in some cases even to sterilize surfaces of objects. This method is based on the ability of short wavelength ultraviolet light to disrupt the biochemical structure of viruses, bacteria and mold.

Due to a minimum exposure time of the surfaces to the short wavelength ultraviolet light required to ensure a sufficient degree of disinfection, decontamination or even sterilization, ultraviolet germicidal irradiation of individual surfaces may constitute a very time consuming process, especially when relatively large numbers of objects, e.g., large numbers of face masks, are to be disinfected, decontaminated and/or sterilized.

Whereas this method can be effectively applied with respect to essentially flat surfaces, the irradiation of three-dimensional objects may constitute a more difficult task. This is particularly so, when objects having different geometries, e.g., face masks of various different shapes, are to be disinfected, decontaminated or even to be sterilized. One of the reasons for this difficulty is, that three-dimensional objects normally include a number of surface areas facing in various directions. Thus, depending on the shape of the object to be irradiated and the position of the ultraviolet light source, there is always a possibility, that one or more surface areas of the object are shadowed by at least a portion of the object itself with respect to the ultraviolet light provided by the ultraviolet light source. Shadowed surface areas will not be fully illuminated, which in turn may result in an insufficient disinfection, decontamination and/or sterilization of the object.

Accordingly, there remains a need for further contributions in this area of technology. As an example, there is a need for a system for ultraviolet irradiation of objects that enables irradiating larger numbers of objects in a time efficient manner.

As another example, there is a need for a system enabling a sufficient degree of disinfection, decontamination or even sterilization of multiple or all surface areas of the objects to be treated, in particular with respect to at least one of: three-dimensional objects, objects given by faces masks and objects given by medical protective equipment.

SUMMARY

The present disclosure discloses a system for ultraviolet irradiation of objects, the system comprising: an illuminating device positioned in a center section of an octagon shaped base area and including one or more elongated light sources, wherein each elongated light source is configured to transmit ultraviolet light given by shortwave ultraviolet light (UV-C light) along its length with an essentially cylindrical symmetrical beam distribution, and wherein each light source extends in parallel to a normal on the base area; a set of rotatable mesh grids arranged around the base area such that the mesh grids surround the illuminating device and configured to be equipped with the objects; and a set of reflectors including a set of movable side reflectors, wherein the reflectors are configured to be arranged such, that they form a resonator surrounding the mesh grids surrounding the illuminating device.

The system provides the advantage, that it allows for a large number of objects accommodated on the mesh grids to be simultaneously irradiated by the ultraviolet light provided by the illuminating device positioned in the center section of the base area. Thus, the system enables for irradiating large numbers of objects to be irradiated in a very time efficient manner.

In addition, the combination of each elongated light source providing ultraviolet along its height and with an essentially cylindrical symmetrical beam distribution and the movable side reflectors reflecting incident ultraviolet light back into an interior of the resonator surrounded by the movable side reflectors provides the advantage of an essentially omnidirectional beam distribution within the interior of the resonator. This provides the advantage, that it prevents most or all of the surfaces areas of the objects forming the front sides of the objects facing the illuminating device from being overshadowed by other surfaces of the objects, regardless of their orientation and position. At the same time, at least some of the ultraviolet light will be reflected onto surface areas of the objects forming the back sides of the objects facing away from the illuminating device under a multitude of different direction.

In particular in applications, where the reflected ultraviolet light illuminating the back sides of the objects may be insufficient to ensure a desired degree of disinfection, the open structure of the mesh grids provides the advantage, that it enables consecutively irradiating multiple sides, e.g. the front sides and the back sides, of the objects. In this respect, the rotatable mesh grids provide the advantage, that consecutive irradiations of different sides of the objects can be performed in a time efficient manner, in a particular without requiring for the individual objects to be released form the mesh grids. In addition, the open grid structure of the mesh grids provides the advantage, that the objects can be accommodated on the mesh grids such, that essentially all sides of the objects are exposed.

An additional advantage of the system is that the movable side reflectors enable easy access to the mesh grids for mounting and dismounting the objects and that they protect people and the environment from exposure to ultraviolet light when they are arranged around the mesh grids during irradiation of the objects.

In addition, the practical design of the system makes the system very easy to use and well suited to be operated by users, e.g. medical technical technicians working in hospitals.

In an embodiment at least one of the one or more elongated light sources of the illuminating device: is or includes an ultraviolet light tube, a fluorescent light tube or a line light source; or includes a linear array of ultraviolet light sources, a linear array of semiconductor light sources, a linear array of solid-state sources, a linear array of light emitting diodes (LED) or a linear array of laser diodes.

In first embodiments, the one or more elongated light sources of the illuminating device include: a single elongated light source positioned in a center of the base area; or a set of four elongated light source arranged in a square array; or a set of eight elongated light source arranged in an octagonal array; or a first set of four elongated light sources arranged in a first square array and a second set of four elongated light sources arranged in a second square array; or a set of four elongated light sources arranged in a square array and a set of eight elongated light sources arranged in an octagon array.

In certain embodiments of the first embodiments:
the four elongated light sources included in the set of four elongated light sources or the four elongated light sources included the first set of four elongated light source are positioned such, that: a) the distances between each of these elongated light source and a center of the base area are identical, b) they are spaced apart from each other by a distance or a distance of 30 cm, wherein the distance corresponds to a side length of the square formed by the array they are arrange in; and/or c) the square array is orientated such, that each of the sides of the square defined by the square array extends in parallel to one of the sides of the octagon of the octagon base area; and/or:
the eight elongated light sources included in the set of eight elongated light sources are positioned such, that: a) each of the eight elongated light sources is spaced apart from a center of the base area by a distance or a distance of 40 cm to 60 cm, wherein the distance corresponds to half the distance between the center of the base area and the mesh grids, and/or b) the octagon array is orientated such, that each of the sides of the octagon defined by the octagon array extend in parallel to one of the sides of the octagon of the octagon base area.

In further embodiments of the first embodiments including the first set of four elongated light sources arranged in the first square array and the second set of four elongated light sources arranged in the second square array:
the elongated light sources belonging to the second set of four elongated light sources are positioned such, that the distances between each of the elongated light source of the second set of four elongated light sources and the center of the base area are identical and larger than the distances between each of the elongated light source of the first set of four elongated light sources and the center of the base area;
the elongated light sources of the second set of four elongated light sources are spaced apart from each other by a distance corresponding to a side length of a square defined by the second square array, wherein the side length of the second square array is essentially equal to a width of the mesh grids and/or a side length of the octagon of the octagon shaped base area;
the first square array and the second square array are each orientated such, that each of the sides of the respective square extends in parallel to one of the sides of the octagon shaped base area; and/or
the first square array and the second square array are each orientated such, that the orientation of the square described by the first array deviates from the orientation of the second square described by the second array by an angle of rotation of 45° around an axis of rotation extending through the center of the base area.

In certain embodiments, a distance between the objects mounted on the mesh grids and a center of the base area is 80 cm to 100 cm.

In certain embodiments, the mesh grids are rotatably mounted on a frame surrounding the base area, the frame including: a set of posts, wherein each post is placed in a position corresponding to one of the corners of the octagon shape of the base area and extends in parallel to each of the one or more elongated light sources; and a set of connecting elements interconnecting upper ends of the posts such, that each connecting element connects the upper ends of two of the posts located next to each other; and each mesh grid either includes a first extension that is rotatably secured to a middle section of one of the connecting elements or includes a first extension that is rotatably secured to a middle section of one of the connecting elements and a second extension located opposite the first extension and rotatably secured to a base plate.

In some embodiments, the mesh grids include fixtures for mounting the objects in grid fields of the mesh grids such, that the objects are essentially fully exposed to their surrounding on all sides.

In certain embodiments, the mesh grids are configured to be: rotated by an angle of rotation of 180° enabling for irradiating a front side and back side of each object mounted on the mesh grids; rotated in steps of angles of rotation of 30° for covering a full rotational; or continuously rotated during irradiation of the objects.

In a further embodiment, the illuminating device is configured to emit ultraviolet light having wavelength(s) of 200 nm to 280 nm; or the one or more elongated light sources are line light source configured to emit an ultraviolet light line light spectrum given by or including a wavelength of 254 nm.

In another embodiment, the system is configured to perform at least one of: subjecting the objects mounted on the mesh grid to a radiation dose of 6 mJ/cm$^2$ to 60 J/cm$^2$ during exposure to the ultraviolet light emitted by the illuminating device; and irradiating the objects on the mesh grids during an exposure time of 1 minute to 15 minutes.

In a further embodiment, the one or more elongates light sources of the illuminating device are each mechanically mounted between a mounting base positioned in a center section of the base area and a light source support suspended above the base area or a light source support suspended above the base area by being attached to at least one frame member of a frame surrounding the base area, wherein the least one frame member extends across a cross-sectional area spanned by the frame at a height above the base area.

In certain embodiments, the set of reflectors includes at least one of: a top reflector reflecting ultraviolet light and configured to be positioned opposite the base area above the one or more elongated light sources; and a bottom reflector reflecting ultraviolet light and covering at least a fraction of the base area.

In another embodiment, each movable side reflector includes a reflecting panel mounted on a set of wheels; and each reflector panel: is reflecting incident ultraviolet light, is a metal panel, is or includes a sheet of aluminum, consists of an ultraviolet light reflecting material, and/or includes microphotonic structures for enhanced back reflection.

In another embodiment, the system further comprises a base plate having a size corresponding to the size of the base area, wherein: the illuminating device is mounted on a center section of the base plate; and wherein: the base plate is mounted onto a frame surrounding the base area or a frame surrounding the base area is mounted onto the base plate; and/or the base plate is positioned at a height above or equal to a height of a bottom edge of reflector panels of the movable side reflectors.

The present disclosure further discloses a method of using the system disclosed herein, the method comprising the step of using the system to disinfect, to decontaminate and/or to sterilize objects, objects given by face mask or objects given by medical equipment by irradiation with short wavelength ultraviolet light (UV-C light) provided by the illuminating device.

An embodiment of the method comprises at least one of the steps of: using the system to irradiate objects, the objects including at least one of: three-dimensional objects, medical equipment and face masks; and irradiating the objects mounted on the mesh grids such, that a log reduction of at least one of: coronavirus, Covid-19, products from bacteria, fungi, molds and at least one other pathogen is attained.

BRIEF DESCRIPTION OF THE DRAWINGS

The described embodiments and other features, advantages and disclosures contained herein and the manner of attaining them will become apparent, and the present disclosure will be better understood, by reference to the following description of various embodiments of the present disclosure taken in junction with the accompanying drawings, wherein:

FIG. 14 shows a perspective view of elongated light sources mounted between a mounting base and a light source support suspended from above;

FIG. 15A shows a perspective view of a top reflector covering an area spanned by a frame; and FIG. 15B shows a plan view of a top reflector covering an area spanned by a frame.

DETAILED DESCRIPTION

Figure 1:
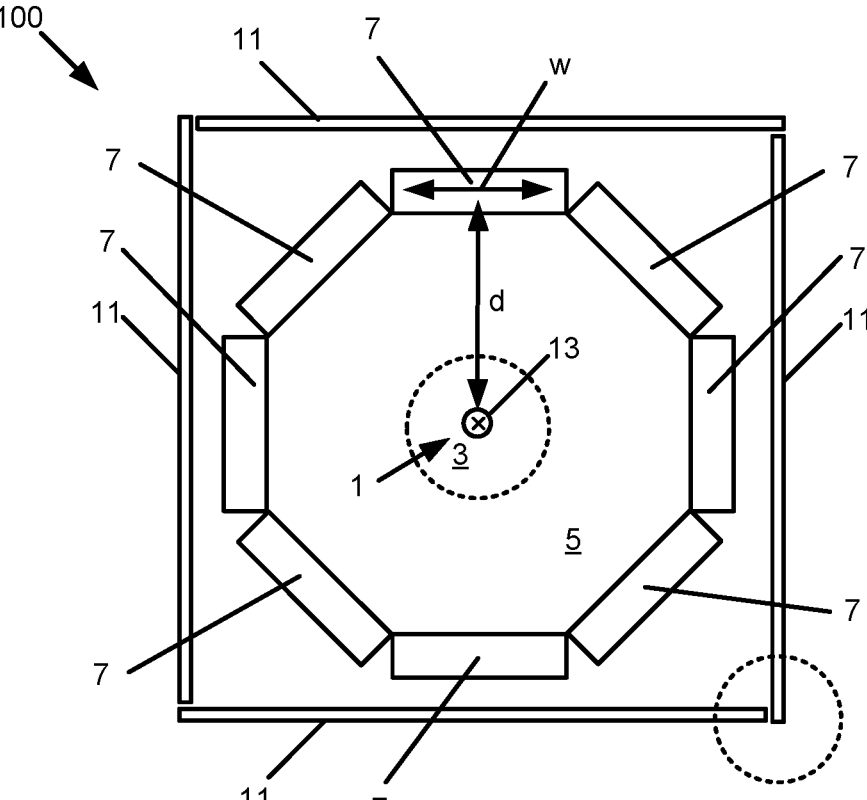
FIG. 1 shows a plan view of a system for ultraviolet irradiation of objects according to the present disclosure.

The present disclosure includes a system 100 for ultraviolet irradiation of objects. An example is shown in FIG. 1. The system 100 includes an illuminating device 1 positioned in a center section 3 of a base area 5, a set of mesh grids 7 configured to be equipped with the objects 9 to be irradiated, and a set of reflectors consisting of or including a set of movable side reflectors 11.

Figure 2:
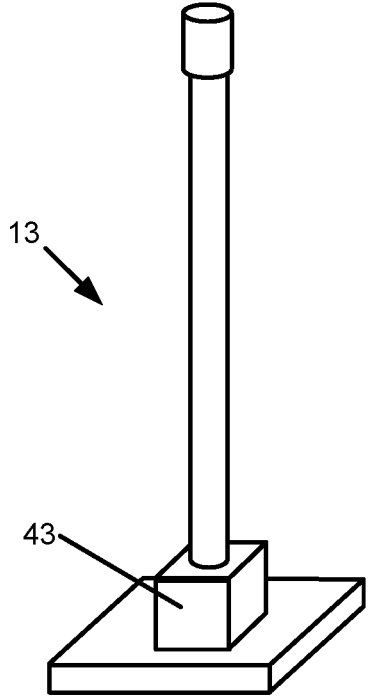
FIG. 2 shows an elongated light source.

The illuminating device 1 includes at least one elongated light source 13. An example of an elongated light source 13 is shown in FIG. 2. Each elongated light source 13 extends parallel to a normal on the base area 5 and is configured to emit ultraviolet light given by short wavelength ultraviolet light (UV-C light) along its length with an essentially cylindrical symmetrical beam distribution.

Elongated light sources 13 suitable for this purpose, e.g., include ultraviolet light tubes, e.g., fluorescent light tubes, and elongated light sources including a linear array of ultraviolet light source, e.g., a linear array of semiconductor light sources, a linear array of solid-state sources, a linear array of light emitting diodes (LED) or a linear array of laser diodes. As an alternative, other types of elongated light sources, e.g., elongated light sources including a linear array of other types of ultraviolet light sources and/or including nonlinear optical devices, configured to emit ultraviolet light along their length with an essentially cylindrical symmetrical beam distribution can be used. In certain embodiments, the elongated light sources 13 may be embodied as line light sources emitting an ultraviolet line light spectrum, e.g., a line light spectrum given by or including a wavelength of 254 nm.

Figures 3, 4:
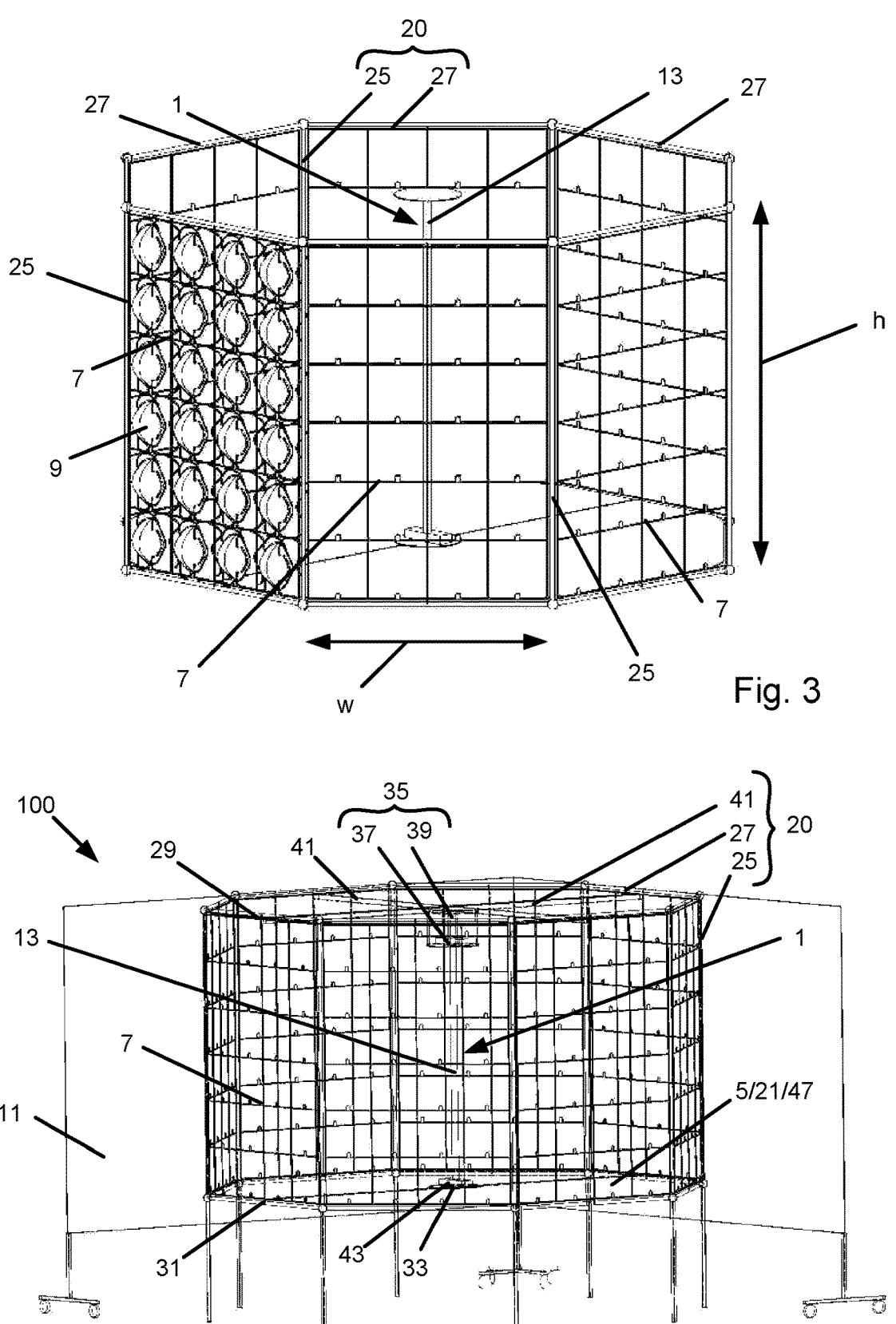
FIG. 3 shows a perspective view of mesh grids mounted on an open frame structure.
FIG. 4 shows a perspective view of rotatable mesh grids surrounding an illuminating device.

As shown in FIG. 1, the mesh grids 7 are configured to be arranged along a perimeter of the base area 5 such that they surround the illuminating device 1. FIG. 3 shows a side view of an embodiment in which the mesh grids 7 are each mounted in a section of an open frame structure, e.g., a frame 20, surrounding the illuminating device 1, and one of the mesh grids 7 is equipped with objects 9. FIG. 4 shows an example of a perspective view of a set of mesh grids 7 rotatably mounted on the frame 20 surrounding the illuminating device 1.

Figure 5:
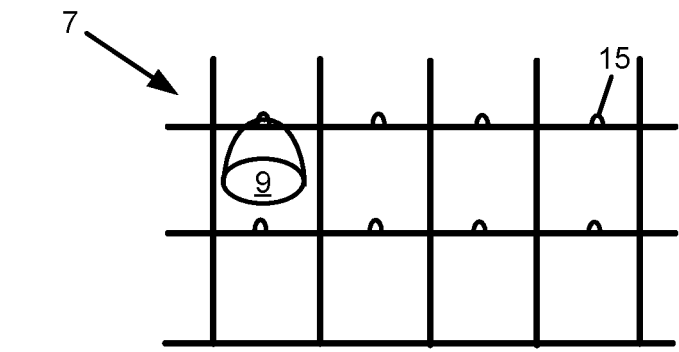
FIG. 5 shows a detail view of a section of a mesh grid.

An embodiment of a detail section of one of the mesh grids 7 is shown in FIG. 5. Each mesh grid 7 may include an array of grid fields configured to be equipped with the objects 9 to be irradiated. As shown, the mesh grid 7 may include horizontal and vertical grid bars forming an open grid structure, e.g., a metal frame, for accommodating the objects 9 and defining a plurality of the grid fields. In certain embodiments, the mesh grids 7 may include fixtures 15 for mounting the objects 9 in the grid fields. As an example, the fixtures 15 may embodied in the form of clips for clipping the objects 9 onto the mesh grids 7 such that each of the objects 9 is suspended from one of the grid bars. An exemplary object 9, here given by a face mask, is shown in FIG. 5. The face mask is suspended from one of the grid bars by one of its straps being held by one of the fixtures 15. One having the benefit of the present disclosure will understand that other types of suitable fixtures may be used, including but not limited to hooks, clamps, fasteners and/or holders configured to enable attaching the objects 9 to be irradiated to the mesh grids 7 such that the objects 9 are essentially fully exposed to their surroundings on all sides.

The set of reflectors including the set of movable side reflectors 11 is configured to be arranged such that the reflectors 11 form a resonator surrounding the mesh grids 7 surrounding the illuminating device 1. To this extent, the movable side reflectors 11 are configured to be arranged around the outside (e.g., opposite the illuminating device 1) of the mesh grids 7 surrounding the illuminating device 1. In this respect, the side reflectors 11 are embodied, e.g., dimensioned, such that they can be arranged to form side walls surrounding an interior of the resonator. In the embodiment shown in FIG. 1, the set of reflectors consists of four movable side reflectors 11 configured to be arranged generally in a square, such that they form four side walls of a generally tubular resonator, though not purely cylindrical, surrounding the mesh grids 7 surrounding the illuminating device 1.

Figure 6:
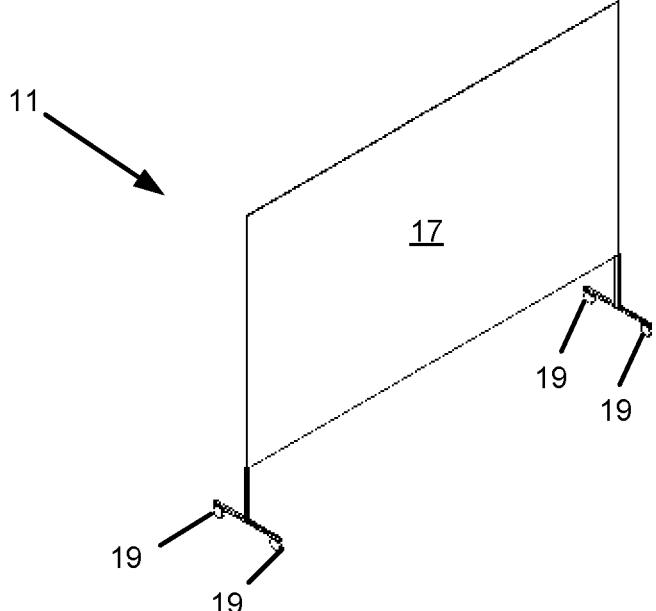
FIG. 6 shows a movable side reflector.

An example of a movable side reflector 11 is shown in FIG. 6. Each movable side reflector 11 may include a reflecting panel 17 adapted for reflecting incident ultraviolet light. As shown in FIG. 6, movability of the side reflector 11 may be facilitated by a set of wheels 19 upon which the reflecting panel 17 may being mounted to enable each side reflector 11 to be rolled into place. In certain embodiments, the set of wheels 19 may be rollers, ball casters, bearings, track or other suitable structure to enable mobility of the reflecting panel 17.

The reflecting panel 17 may be a metal panel. As an example, the reflecting panel 17 is or includes a sheet of aluminum. Sheets of aluminum provide the advantage of being thin and light, which in turn enables the advantage that the movable side reflectors 11 can be easily moved.

Alternative other types of reflecting panels 17, e.g., reflecting panels 17 consisting of or including other types of ultraviolet light reflecting materials, e.g., highly reflective materials, and/or reflecting panels 17 having a different surface structure, e.g., reflecting panels having or including microphotonic structures for enhanced back reflection, can be used. In at least one embodiment, the reflecting panel 17 includes a surface finish or treatment to facilitate and/or enhance reflective properties, e.g., UV-C reflective properties, of the reflecting panel 17, including but not limited to anodizing, vapor deposition or a reflective paint or coating.

Based on the system 100 disclosed herein, a method of using the system 100 includes using the system 100 to disinfect, to decontaminate or even to sterilize the objects 9 by irradiating them with the ultraviolet light provided by the illuminating device 1. In this respect, the objects 9 may include at least one of: three-dimensional objects, medical equipment and face masks.

The method of the present disclosure may include steps of mounting the objects 9 to be irradiated on the mesh grids 7 surrounding the illuminating device 1, arranging the movable side reflectors 11 around the outside of the mesh grids 7 such that side reflectors 11 form side walls of a resonator surrounding the mesh grids 7 surrounding the illuminating device 1 on all sides, and at least once irradiating the objects 9 with ultraviolet light emitted by illuminating device 1.

The method of using the system 100 may include irradiating objects 9, in particular medical equipment and/or face masks, such that a sufficient log reduction of coronavirus, Covid-19, products from bacteria, fungi, molds and/or at least one other pathogen is attained.

The systems and methods of the present disclosure enable the advantages mentioned above. Various embodiments of individual components of the system 100 can be applied without deviating from the scope of the present disclosure. Several embodiments that can be applied individually and/or in combination are described in detail herein.

In the embodiment shown in FIGS. 1, 3 and 4, the base area 5 has the shape of a polygon, e.g., the shape of an octagon. In this case, the set of mesh grids 7 may include a number of mesh grids 7 corresponding to the number of sides of the polygon shape of the base area 5. In the embodiments shown, the set of mesh grids 7 includes eight mesh grids 7 arranged in an octagon, e.g., per the perimeter of the base area 5, around the illuminating device 1.

Figure 7:
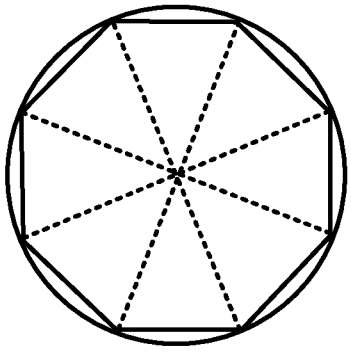
FIG. 7 shows an octagon in a circle.

As illustrated in FIG. 7 showing an octagon in a circle, the octagon shaped arrangement of the mesh grids 7 applied during irradiation provides the advantage that the arrangement replicates the essentially cylindrically symmetrical radiation distribution of the ultraviolet light provided by the elongated light sources 13 of the illuminating device 1 relatively closely. This is particularly advantageous with respect to the full illumination of three-dimensional objects 9, because it leads to a significant reduction or even a complete elimination of surfaces areas of the objects 9 forming the front sides of the objects 9 facing the illuminating device 1 that might otherwise be shadowed by other surface areas of the objects 9 and would therefore only be illuminated by ultraviolet light reflected by the reflectors forming the resonator.

In the embodiments shown, each mesh grid 7 has a width w corresponding or complementary to a side length of the sides of the polygon shaped base area 5 and a height h corresponding or complementary to the length of the elongated light sources 13 of the illuminating device 1. The rectangular shape of the mesh grids 7 provides the advantage that a comparatively large number of objects 9 can be accommodated on each mesh grid 7.

In addition, the grid fields of the mesh grids 7 provide the advantage of enabling illumination of all sides of the objects 9. To this extend various embodiments may by applied.

Depending on properties of the objects 9, e.g., their shape, their material(s) and/or their thickness, and their purpose of use, the irradiation of the back sides of the objects 9 attained by the ultraviolet light reflected onto them by the set of reflectors, including the movable side reflectors 11, may already be sufficient to achieve an acceptable degree of disinfection, decontamination or even sterilization of the objects 9.

In certain embodiments additional measures may be taken or foreseen to attain a higher and/or more homogeneous degree of disinfection, decontamination or even sterilization across all surface areas of the objects 9. As an example, each of the mesh grids 7 may be embodied in form of a rotatable mesh grid 7, e.g., in form of a mesh grid 7 rotatable around an axis of rotation, e.g., an axis of rotation extending parallel to a longitudinal axis of the illuminating device 1, extending parallel to a longitudinal axis of each of the elongated light sources 13. As an example, each mesh grid 7 may be rotatable around an axis of rotation extending parallel to its height h through its center.

In certain embodiments, the system 100 may include the frame 20 surrounding the base area 5. In this case, each of the mesh grids 7 is rotatably mounted on the frame 20. Such embodiments are illustrated in FIGS. 4, 8 and 9, each showing side views of exemplary the mesh grids 7 being rotatably mounted onto the frame 20 surrounding the illuminating device 1, including some of the movable side reflectors 11.

Figure 8:
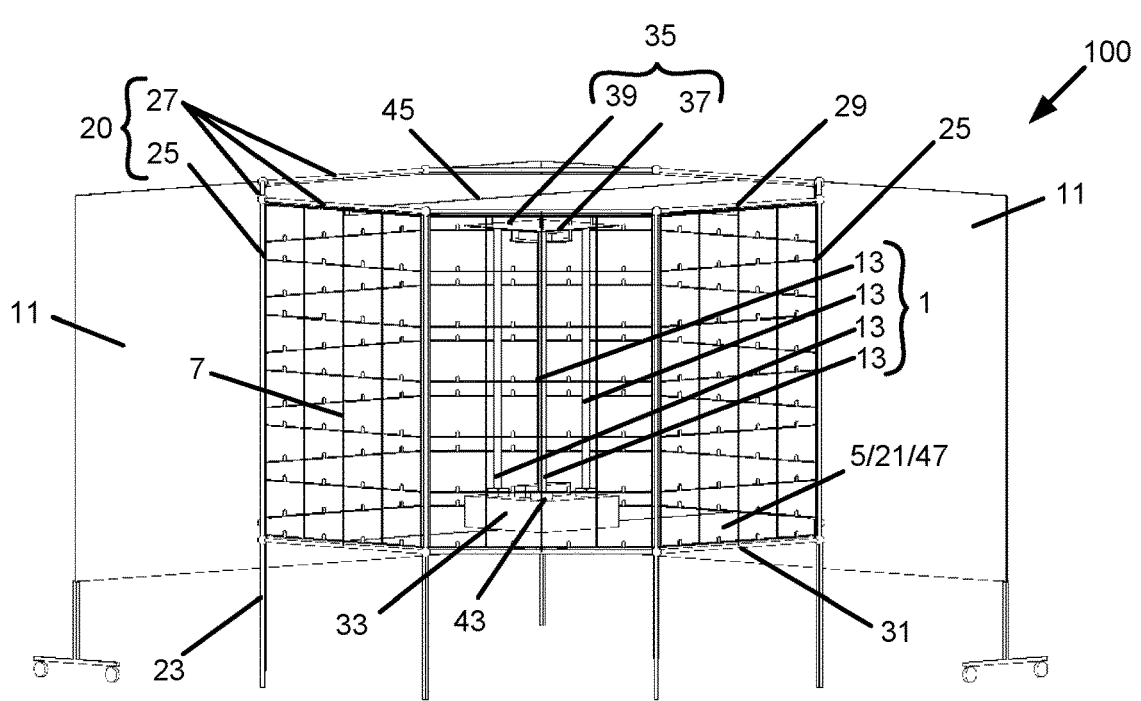
FIG. 8 shows a perspective view of a system according to the present disclosure including rotatably mounted mesh grids.
Figure 9:
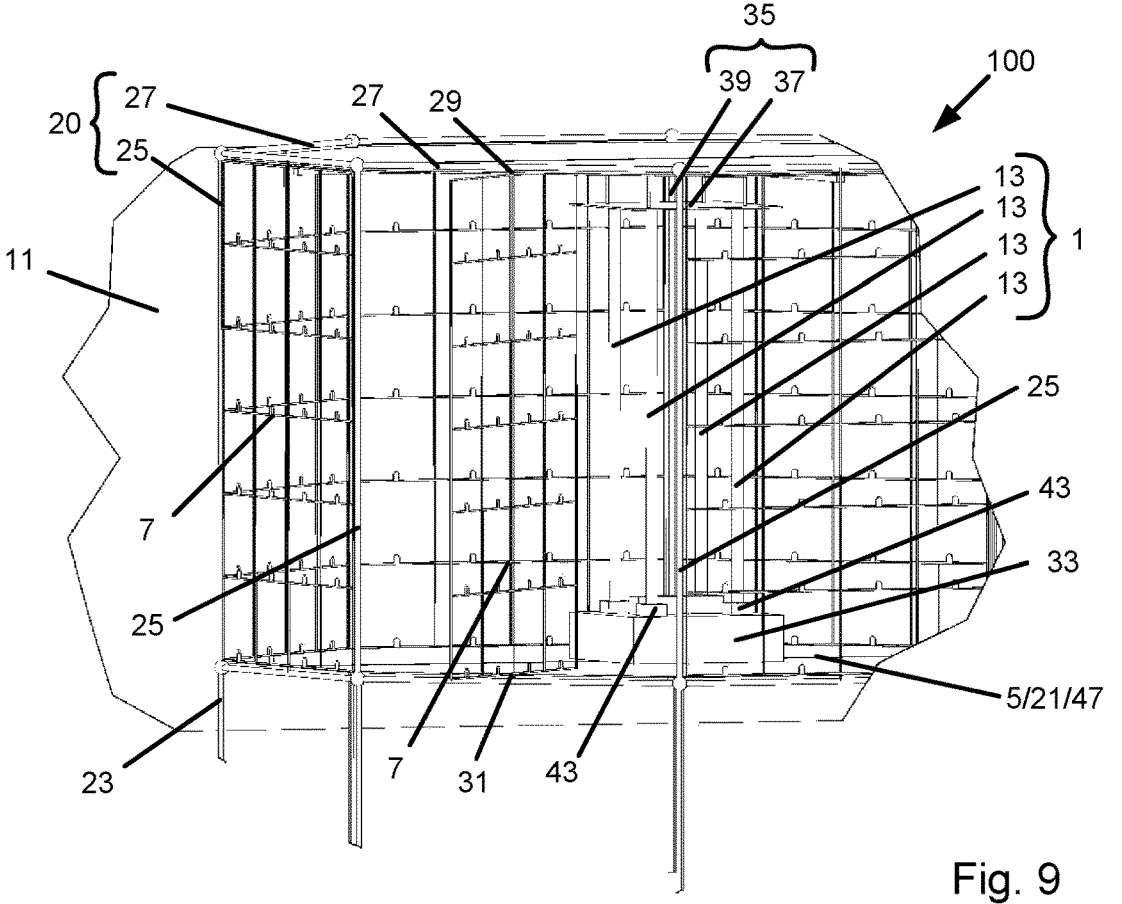
FIG. 9 shows a partial view of the system shown in FIG. 8 with one of the mesh grids rotated into a different position than shown in FIG. 8 for clarity.

In FIG. 4 and FIG. 8, the mesh grids 7 are rotated into a position as to form side walls of the octagon defined by the octagonal shape of the base area 5. In FIG. 9, one of the rotatable mesh grids 7 is rotated into a different position to illustrate the rotatability of the mesh grids 7. In the embodiments shown, each mesh grid 7 is rotatably mounted onto a different frame section of the frame 20.

In certain embodiments, the system 100 may include a base plate 21 having a size corresponding to the size of the base area 5. In such embodiments, the base plate 21 may be mounted onto the frame 20 or vice versa, and the illuminating device 1 may be mounted on a center section of the base plate 21. Further, the base plate 21 may be positioned at a height above or equal to a height of a bottom edge of the reflector panels 17 of the movable side reflectors 11. As shown in FIG. 8, the base plate 21 may be mounted on feet 23 such that the base plate 21 is at a desired height with respect to the reflector panels 17.

As shown, the frame 20 may include a set of posts 25 evenly distributed along an outside contour of the base area 5. The posts 25 may be each disposed in a position corresponding to one of the corners of the polygonal (e.g., octagonal) shape of the base area 5 or the base plate 21, and each post 25 may extend parallel to the elongated light sources 13.

The frame 20 further includes a set of connecting elements 27 interconnecting the upper ends of the posts 25 such that each connecting element 27 connects the upper ends of two of the posts 25 located next to each other.

In the embodiment shown, each mesh grid 7 includes a first extension 29 that is rotatably secured to a middle section of one of the connecting elements 27. In embodiments of the system 100 that include the base plate 21, each mesh grid 7 may include a second extension 31 located opposite the first extension 29 and rotatably secured to the base plate 21. In such an embodiment, the axis of rotation of each mesh grid 7 corresponds to the longitudinal axis of the respective mesh grid 7 extending through the center of the respective mesh grid 7 and the first and the second extension 29, 31.

The rotatable mesh grids 7 enable all objects 9 mounted on the same mesh grid 7 to be rotated simultaneously by rotating the respective mesh grid 7 accordingly. In such embodiments including rotatable mesh grids 7, the method of using the system 100 may include additional steps of at least once rotating the mesh grids 7 during irradiation of the objects 9 or in between consecutive irradiations of the objects 9.

As an example, the mesh grids 7 may each be rotated through an angle of rotation of 180° between consecutive irradiations of the objects 9. The angle of rotation of 180° enables that only two irradiations are needed to expose opposite sides of each object 9, e.g., the front side and the back side, to direct radiation from the illuminating device 1, while the other side is exposed to ultraviolet light reflected from the set of reflectors.

As another example, the mesh grids 7 may each be rotated in steps of smaller angles of rotation, e.g., of angles of rotation of 30°, incrementally applied to cover a full rotational.

In certain embodiments, the method of using the system 100 may include a step of continuously rotating the mesh grids 7 during irradiation of the objects 9.

Rotating the mesh grids 7 at least once or continuously provides the advantage, that a more homogeneous degree of disinfection, decontamination or even sterilization across all surface areas of the objects 9 is attained.

With respect to the function of the irradiation to disinfect, to decontaminate or to sterilize the objects 9, the illuminating device 1 is configured to emit short wavelength ultraviolet light (UV-C light). In certain embodiments, the illuminating device 1 is may be configured to emit ultraviolet light having wavelength of 200 nm to 280 nm. In embodiments in which the elongated light sources 13 include or consist of at least one line light source, each line light source may be configured to emit an ultraviolet light spectrum given by or including a wavelength of 254 nm.

The system 100, in particular the illuminating device 1, may be configured to generate ultraviolet light such that the objects 9 are subjected to a radiation dose of 6 mJ/cm$^2$ to 60 J/cm$^2$ during exposure to the ultraviolet light emitted by the illuminating device 1.

This dose range ensures that the dose applied is sufficiently high to cause a relatively high degree of disinfection, decontamination or sterilization. At the same time the dose range is sufficiently low to avoid impairments of the objects 9 being irradiated, e.g., impairments of a filtration capacity of face masks that may otherwise be caused by the irradiation.

In certain embodiments, the objects 9 may be exposed to the ultraviolet light emitted by the illuminating device 1 during an exposure time of 1 minute to 15 minutes.

In certain embodiments, the system 100 may be configured such that a distance d between the objects 9 mounted on the mesh grids 7 and the center of the base area 5 indicated by an "X" in FIG. 1 is lager or equal to 80 cm and smaller or equal to 100 cm.

As mentioned herein, the illuminating device 1 includes one or more elongated light sources 13 positioned in the center section 3 of the base area 5. The illuminating devices 1 shown in FIGS. 1, 3 and 4, each include a single elongated light source 13 positioned in the center of the base area 5. Such embodiments may be particularly suitable when the objects 9 have an essentially flat shape.

In further embodiments, illuminating devices 1 including more than one elongated light source 13 may be used. Having more than one elongated light source 13 enables each elongated light source 13 to cast ultraviolet light directly onto individual surfaces areas of the objects 9 mounted on the mesh grids 7 surrounding the illuminating device 1 under a different range of angles of incidence. Thus, surfaces areas of the objects 9 that may be shadowed by another surface area with respect to some or all angles of incidence of ultraviolet light emitted by one of the light sources 13 are exposed to the direct ultraviolet light emitted by at least one of the other elongated light sources 13. Embodiments of systems 100 in which the illuminating device 1 includes at least one set of elongated light source 13 arranged in an array are shown in FIGS. 10 to 13.

Figure 10:
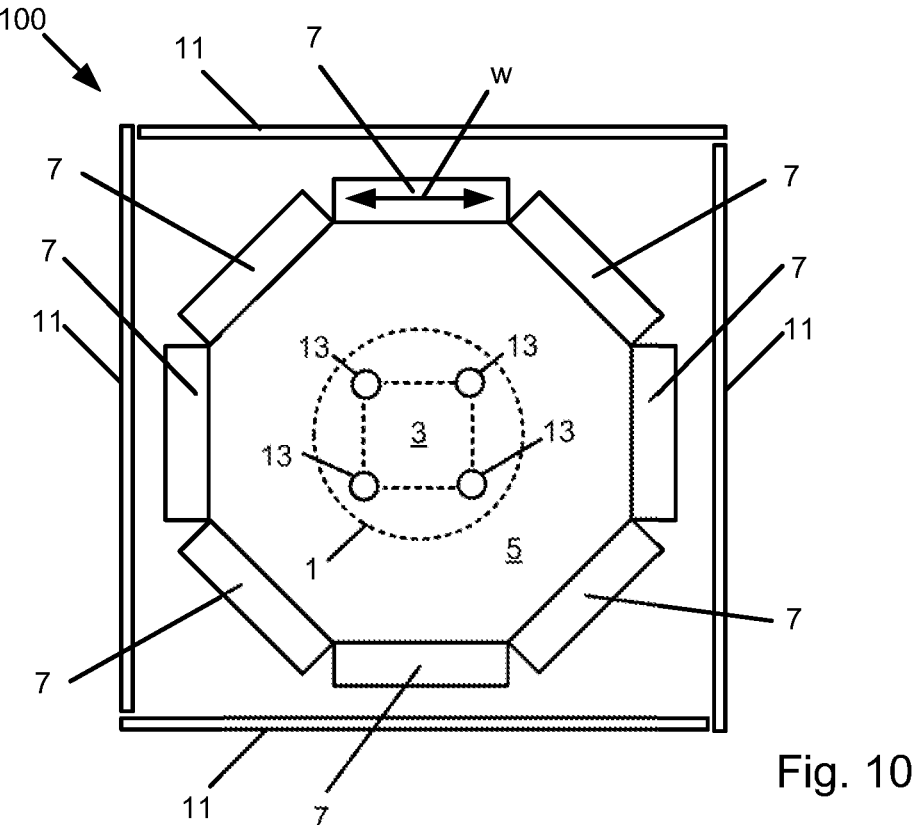
FIG. 10 shows a plan view of a system of the present disclosure including elongated light sources arranged in a square array.

FIGS. 8, 9 and 10 show a modification of the system 100 shown in FIG. 1 in which the illuminating device 1 includes four elongated light sources 13 arranged in a square array. In such an embodiment, the elongated light sources 13 may be all positioned such that the distances between each of the elongated light sources 13 and the center of the base area 5 are identical. As an example, the elongated light sources 13 may be spaced apart from each other by a distance corresponding to a side length of 30 cm of the square array centered at the center of the base area 5. Further, the square array may be orientated such that each of the sides of the square defined by the square array extends parallel to one of the sides of the polygonal or octagonal base area 5.

Figure 11:
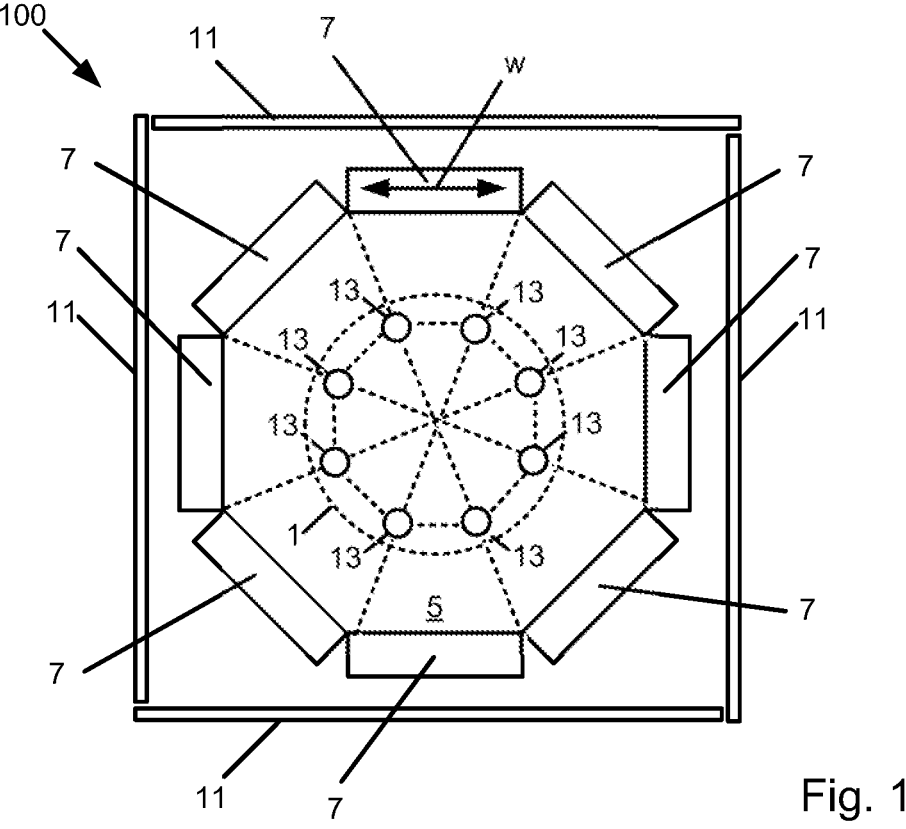
FIG. 11 shows a plan view of a system of the present disclosure including elongated light sources arranged in an octagon array.

FIG. 11 shows an alternative embodiment in which the illuminating device 1 includes eight elongated light sources 13 arranged in an octagonal array. Like in the previous embodiment, the elongated light sources 13 may be each positioned such that the distances between each of the elongated light sources 13 and the center of the base area 5 are identical. As shown, the octagonal array may be orientated such that each of the sides of the octagon defined by the octagon array extend parallel to one of the sides of the octagon base area 5. As an example, the eight elongated light sources may be each spaced apart from the center of the base area 5 by a distance corresponding to half the distance between the center of the base area 5 and the mesh grids 7. As an example, the elongated light sources may be disposed at distance of 40 cm to 60 cm from the center of the base area 5.

In certain embodiments, the illuminating device 1 may include two or more sets of elongated light sources 13 in which the elongated light sources 13 belonging to the same set are arranged in an array.

Figure 12:
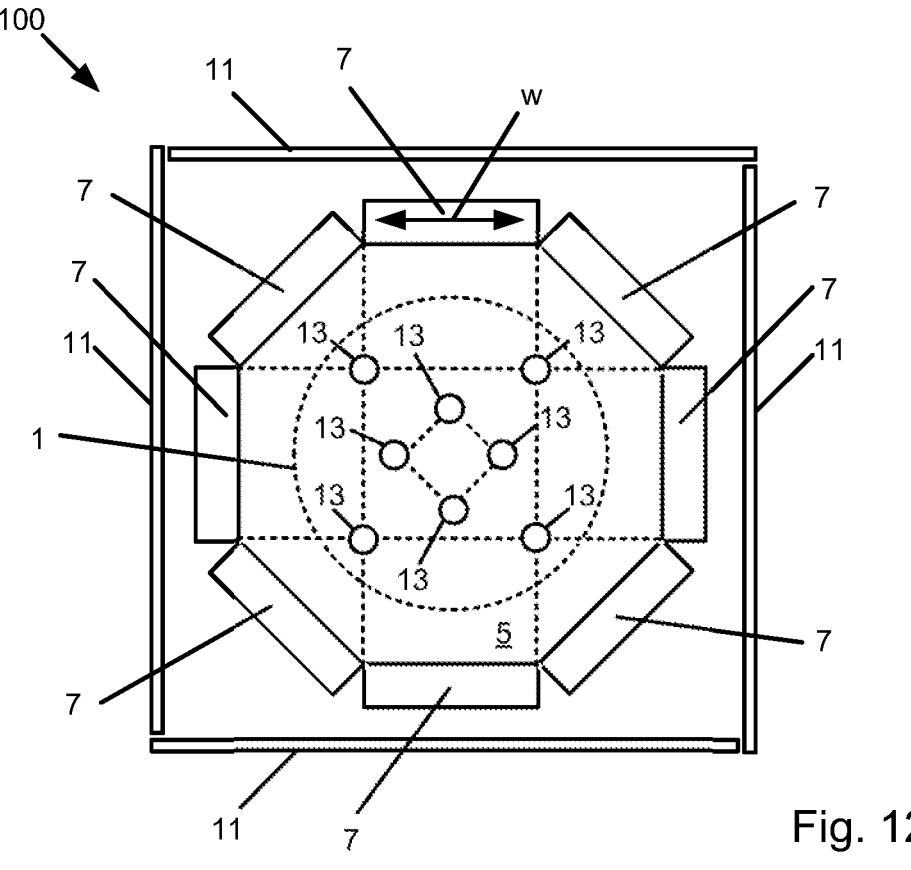
FIG. 12 shows a plan view of a system of the present disclosure including a first set of elongated light sources arranged in a first square array and a second set of elongated light sources arranged in a second square array.

FIG. 12 shows an embodiment in which the illuminating device 1 includes a first set of four elongated light sources 13 and a second set of four elongated light sources 13. The elongated light sources 13 belonging to the first set may be arranged in a first square array and may be positioned such that the distances between each of the elongated light source 13 of the first set and the center of the base area 5 are identical. As an example, the elongated light sources 13 of the first set may be spaced apart from each other by a distance corresponding to the side length of the square array of 30 cm. The elongated light sources 13 of the second set are arranged in a second square array and may be positioned such that the distances between each of the elongated light source 13 of the second set and the center of the base area 5 are identical and larger than the distances between each of the elongated light source 13 of the first set and the center of the base area 5. The elongated light sources 13 of the second set may be spaced apart from each other by a distance corresponding to a side length of the square defined by the second square array. The side length of the square defined by second square array may be at least approximately equal to the width w of the mesh grids 7 and/or the side length of the octagon of the octagonal base area 5. In such an embodiment, the first and the second square array may be each orientated such that each of the sides of the squares defined by the first and the second square array extends parallel to one of the sides of the polygon base area 5 and/or such that the orientation of the square defined by the first array deviates from the orientation of the square defined by the second array by an angle of rotation around an axis of rotation extending through the center of the base area 5 of around 45°.

Figure 13:
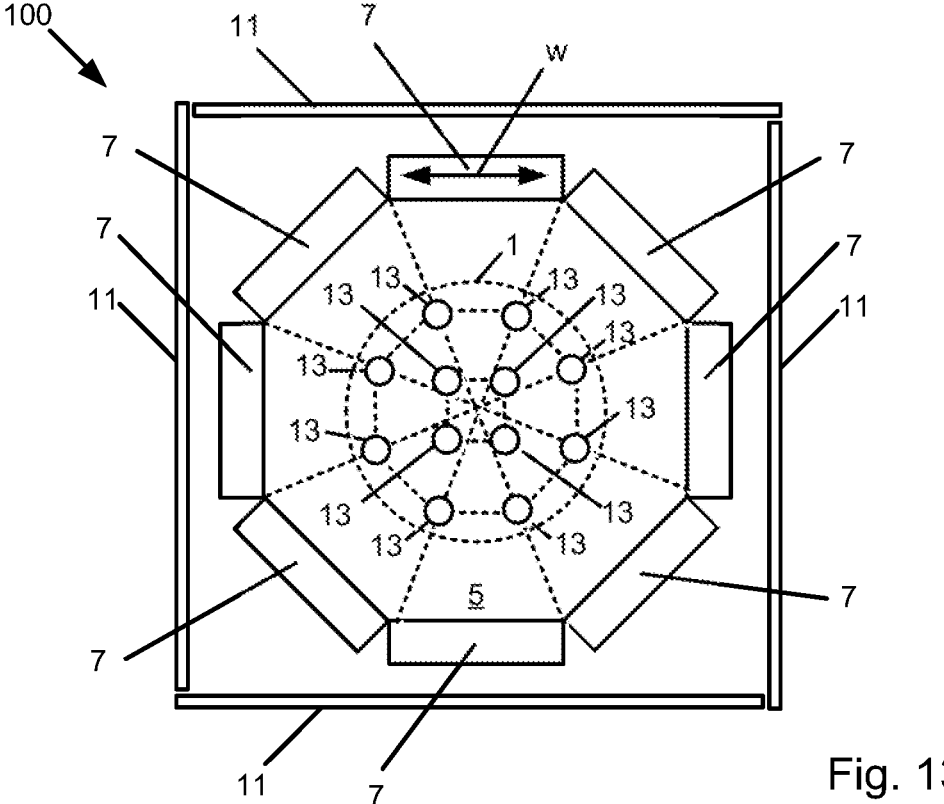
FIG. 13 shows a plan view of a system of the present disclosure including a set of four elongated light sources arranged in a square array and a set of eight elongated light sources arranged in an octagon array.

FIG. 13 shows an alternative embodiment in which the illuminating device 1 includes a set of four elongated light sources 13 and a set of eight elongated light sources 13. In such an embodiment, the elongated light sources 13 of the set of four elongated light sources 13 may be positioned and arranged as described with respect the embodiment shown in FIG. 10. In addition or as an alternative, the elongated light sources 13 of the set of eight elongated light sources 13 may be positioned and arranged as described above with respect the embodiment shown in FIG. 11.

Regardless of the number of elongates light sources 13 included in the illuminating device 1, each elongated light source 13 may be mechanically mounted between a mounting base 33 and a light source support 35 suspended above the base area 5 as shown in FIGS. 8, 9 and 14. The mounting base 33 and light source support 35 enable the elongated light sources 13 to be mounted such that the area surrounding the elongated light sources 13 along their entire length is free of mounting means, which would otherwise intersect at least some of the emission paths of the cylindrically symmetrical beam distributions of the ultraviolet light transmitted by the elongated light sources 13.

FIG. 14 shows an embodiment of the illuminating device 1 including four elongated light sources 13 in which each elongated light source 13 is clamped in between the mounting base 33 and the light source support 35 configured to be suspended from above.

In such embodiments, the light source support 35 may include a plate 37 and a fastening device 39 mounted onto a side of the plate 37 facing away from the elongated light sources 13 and configured to enable for the light source support 35 to be suspended from above.

Examples of the light source support 35 being suspended from above are shown in FIGS. 4, 8 and 9. In the examples shown, the suspension of the light source support 35 is attained by the light source support 35 being mounted onto the frame 20 by the fastening device 39. To this extent, as shown for example in FIG. 4, the frame 20 may include one or more frame members 41, e.g., cross beams, extending across a cross-sectional area spanned by the frame 20 at a height corresponding to the height at which the light source support 35 is to be suspended above the base area 5. In this case, the light source support 35 may be attached to the frame member(s) 41 extending above the light source support 35 by the fastening device 39. In alternative embodiments, other mechanical means for suspending the light source support 35 from above may be used.

Suspending the light source support 35 from above (e.g., by mounting it onto the frame 20) enables the weight of the light source support 35 to be supported by the frame 20. This configuration provides the advantage that the elongated light sources 13 can be connected between the mounting base 33 and the light source support 35 and that none of the elongated light sources 13 must carry any of the weight of the light source support 35.

In the embodiment shown in FIG. 14, each of the elongated light sources 13 is mounted on a mounting block 43 foreseen on the mounting base 33.

As described herein, during irradiation of the objects 9, the ultraviolet light emitted by the illuminating device 1 is reflected by the movable side reflectors 11 arranged around the mesh grids 7. As illustrated in the circled section of FIG. 1, during irradiation the movable side reflectors 11 may be positioned such that a lateral side face of each of the movable side reflectors 11 is facing an outer edge of a front surface of the adjacent movable side reflector 11. This arrangement provides the advantage that it minimizes leakage of ultraviolet light escaping an inner volume of the tubular resonator defined by the movable side reflectors 11.

Each elongated light source 13 of the illuminating device 1 transmits ultraviolet light with an essentially cylindrically symmetrical beam distribution. Considering a single spatial direction covered by the cylindrically symmetrical beam distribution, the ultraviolet light rays emitted in this spatial direction include rays emitted along transmission paths covering a range of inclination angles relative to a horizontal. With the system 100 as shown in FIG. 1, where the movable side reflectors 11 are arranged to define the side walls of the tubular resonator, most of the ultraviolet light emitted by the illuminating device 1 will be contained inside the tubular resonator. Nonetheless, the transmission paths may include transmission paths extending along straight lines crossing the positions of the movable side reflectors 11 at a height exceeding the height of the movable side reflectors 11, and transmission paths extending along straight lines pointing towards the base area 5 of the system 100.

In certain embodiments, the efficiency of the irradiation of the objects 9 may be further increased and/or an increasingly omnidirectional beam distribution of the ultraviolet light irradiating the objects 9 may be attained by a set of reflectors configured to form the resonator additionally including at least one of: a top reflector 45, reflecting ultraviolet light and configured to be positioned opposite the base area 5 above the elongated light source 13, and a bottom reflector 47, reflecting ultraviolet light and covering at least a fraction of the base area 5. In such an embodiment, the top reflector 45 and/or the bottom reflector 47 may be embodied as metal reflectors. In alternative embodiments, another type of reflector configured to reflect the ultraviolet light can be used as top reflector 45 and/or as bottom reflector 47 instead.

An embodiment of the top reflector 45 configured to cover an area spanned by mesh grids 7 surrounding the illuminating device 1 and mounted on the frame 20 is shown in FIGS. 15A and 15B. As shown, the top reflector 45 may be embodied as a top cover configured to be positioned or mounted onto the frame 20 at a position opposite the base area 5 and at a height exceeding the height of the elongated light sources 13 such that the top reflector 45 covers at least a fraction or all of the base area 5.

In certain embodiments, the top reflector 45 may include or consist of more than one individual reflector elements 49, 51. In the embodiment shown in FIGS. 15A and 15B, the top reflector 45 includes two disk-shaped reflector elements 49, 51, each having a semicircular disk area.

Individual reflector elements 49, 51 may to facilitate the installation of the top reflector 45 in place. In addition, individual reflector elements 49, 51 may facilitate accommodating parts of the system 100, e.g., parts of the frame 20 extending across the base area 5 and/or parts required for mounting and/or for wiring up the elongated light sources 13, e.g., the light source support 35 attached to the frame 20 and/or connecting wires that may be guided through an opening 53 between individual reflector elements 49, 51.

In the embodiment shown in FIG. 8, the top reflector 45 is embodied as a ceiling resting on or attached to the frame 20.

The bottom reflector 47 may be embodied as a bottom cover configured to be positioned opposite the top reflector 45 on the base area 5. In the embodiments shown in FIGS. 4, 8 and 9, the bottom reflector 47 is embodied as a bottom cover covering the base plate 21.

Systems including at least one of the top reflector 45 and the bottom reflector 47 enable the ultraviolet light reflected back into the resonator by the respective reflector during irradiation to increase the efficiency of the resonator and to generate an even more omnidirectional beam distribution of the ultraviolet light the objects 9 are exposed to during irradiation.

While various embodiments of a system for ultraviolet irradiation of objects and methods for using and constructing the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. The present disclosure is not intended to be exhaustive or to limit the scope of the subject matter of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and thus remain within the scope of the present disclosure.

LIST OF REFERENCE NUMERALS

1 Illuminating device
3 Center section
5 Base area
7 Mesh grids
9 Object
11 Movable side reflectors
13 Elongated light source
15 Fixtures
17 Reflecting panel
19 Wheels
20 Frame
21 Base plate
23 Feet
25 Posts
27 Connecting elements
29 First extension
31 Second extension
33 Mounting base
35 Light source support
37 Plate
39 Fastening device
41 Frame member
43 Mounting block
45 Top reflector
47 Bottom reflector
49 Reflector elements
51 Reflector elements
53 Opening
100 System

The invention claimed is:

1. A system for ultraviolet irradiation of a plurality of objects, the system comprising:

an illuminating device disposed in a center section of an octagon-shaped base area and including one or more elongated light sources, wherein each elongated light source is configured to emit ultraviolet light of a short wavelength along a length of the respective elongated light source with an essentially cylindrical symmetrical beam distribution, and wherein each elongated light source extends parallel to a normal of the base area;

a set of rotatable mesh grids arranged around the base area such that the mesh grids surround the illuminating device, wherein each mesh grid includes an array of grid fields, each grid field including a fixture given by a clamp, a hook, a fastener, or a holder and configured to enable mounting at least one of the plurality of objects in a respective grid field such that the at least one object is essentially fully exposed to its surroundings on all sides; and a set of reflectors including a set of movable side reflectors, wherein the reflectors are configured to be arranged as to form a resonator surrounding the set of mesh grids surrounding the illuminating device.

2. The system of claim 1, wherein at least one of the one or more elongated light sources of the illuminating device:

is or includes an ultraviolet light tube, a fluorescent light tube or a line light source; or includes a linear array of ultraviolet light sources, a linear array of semiconductor light sources, a linear array of solid-state sources, a linear array of light emitting diodes (LED) or a linear array of laser diodes.

3. The system of claim 1, wherein the one or more elongated light sources of the illuminating device comprise:

a single elongated light source disposed in a center of the base area; or a set of four elongated light sources arranged in a square array; or a set of eight elongated light sources arranged in an octagonal array; or a first set of four elongated light sources arranged in a first square array and a second set of four elongated light sources arranged in a second square array; or a set of four elongated light sources arranged in a square array and a set of eight elongated light sources arranged in an octagonal array.

4. The system of claim 3, wherein the four elongated light sources included in the set of four elongated light sources or the four elongated light sources included in the first set of four elongated light sources are positioned such that:

a) the distances between each of the four elongated light sources and a center of the base area are identical;

b) the four elongated light sources are spaced apart from each other by a distance or a distance of 30 cm, wherein the distance corresponds to a side length of a square formed by the square array in which elongated light sources are arranged; and/or c) the square array is orientated such that each side of the square defined by the square array extends parallel to one side of an octagon of the octagonal base area; and/or wherein the eight elongated light sources included in the set of eight elongated light sources are positioned such that:

a) each of the eight elongated light sources is spaced apart from a center of the base area by a distance or a distance of 40 cm to 60 cm, wherein the distance corresponds to half the distance between the center of the base area and the mesh grids; and/or b) the octagonal array is orientated such that each side of an octagon defined by the octagonal array extends parallel to one side of the octagon of the octagonal base area.

5. The system of claim 3, comprising the first set of four elongated light sources arranged in the first square array and the second set of four elongated light sources arranged in the second square array, wherein:

the elongated light sources of the second set of four elongated light sources are disposed such that the distances between each elongated light source of the second set of four elongated light sources and the center of the base area are identical and larger than the distances between each elongated light source of the first set of four elongated light sources and the center of the base area;

the elongated light sources of the second set of four elongated light sources are spaced apart from each other by a distance corresponding to a side length of a square defined by the second square array, wherein the side length of the second square array is essentially equal to a width of the mesh grids and/or a side length of the octagon of the octagon-shaped base area;

the first square array and the second square array are each orientated such that each side of each respective square extends parallel to one side of the octagon-shaped base area; and/or the first square array and the second square array are each orientated such that an orientation of the square described by the first array deviates from an orientation of the second square described by the second array by an angle of rotation of 45° around an axis of rotation extending through the center of the base area.

6. The system of claim 1, wherein a distance between any of the plurality of objects mounted on the mesh grids and a center of the base area is 80 cm to 100 cm.

7. The system of claim 1, wherein the mesh grids are rotatably mounted on a frame surrounding the base area, the frame comprising:

a set of posts, wherein each post is placed in a position corresponding to one of the corners of the octagon shape of the base area and extends parallel to each of the one or more elongated light sources;

a set of connecting elements interconnecting upper ends of the posts such that each connecting element connects the upper ends of two adjacent posts; and each mesh grid either includes a first extension that is rotatably secured to a middle section of one of the connecting elements or includes a first extension that is rotatably secured to a middle section of one of the connecting elements and a second extension located opposite the first extension and rotatably secured to a base plate.

8. The system of claim 1, wherein the mesh grids are configured to be:

rotated by an angle of rotation of 180° as to enable irradiating a front side and back side of each object mounted on the mesh grids;

rotated in steps of angles of rotation of 30° through a full rotation; or continuously rotated during irradiation of the objects.

9. The system of claim 1, wherein:

the illuminating device is configured to emit ultraviolet light having wavelength(s) of 200 nm to 280 nm; or the one or more elongated light sources are line light sources configured to emit an ultraviolet light line light spectrum given by or including a wavelength of 254 nm.

10. The system of claim 1, wherein the system is configured to perform at least one of:

subjecting the objects mounted on the mesh grid to a radiation dose of 6 mJ/cm² to 60 J/cm² during exposure to the ultraviolet light emitted by the illuminating device; and irradiating the objects on the mesh grids during an exposure time of 1 minute to 15 minutes.

11. The system of claim 1, wherein the one or more elongated light sources of the illuminating device are each mechanically mounted between a mounting base disposed in a center section of the base area and a light source support suspended above the base area by being attached to at least one frame member of a frame surrounding the base area, wherein the least one frame member extends across a cross-sectional area spanned by the frame at a height above the base area.

12. The system of claim 1, wherein the set of reflectors includes at least one of:

a top reflector adapted to reflect ultraviolet light and configured to be positioned opposite the base area above the one or more elongated light sources; and a bottom reflector adapted to reflect ultraviolet light and configured to cover at least a fraction of the base area.

13. The system of claim 1, wherein:

each movable side reflector includes a reflecting panel mounted on a set of wheels; and each reflector panel is adapted to reflect incident ultraviolet light, is a metal panel, is or includes a sheet of aluminum, consists of an ultraviolet light reflecting material, and/or includes microphotonic structures for enhanced back reflection.

14. The system of claim 1, further comprising a base plate having a size corresponding to the size of the base area, wherein:

the illuminating device is mounted on a center section of the base plate; and wherein:

the base plate is mounted onto a frame surrounding the base area or a frame surrounding the base area is mounted onto the base plate; and/or the base plate is disposed at a height above or equal to a height of a bottom edge of the reflector panels of the movable side reflectors.

15. A method of disinfecting, decontaminating and/or sterilizing objects, the method comprising:

disinfecting, decontaminating and/or sterilizing objects by irradiating the objects with short wavelength ultraviolet light provided by the illuminating device of the system according to claim 1.

16. The method of claim 15, further comprising at least one of:

using the system to irradiate the objects, wherein the objects include at least one of medical equipment and face masks; and irradiating the objects mounted on the mesh grids such that a log reduction is attained of at least one of: coronavirus, Covid-19, products from bacteria, fungi, molds, or another pathogen.

17. A system for ultraviolet irradiation of a plurality of objects, the system comprising:

an irradiating device disposed in a center section of a base area and including one or more elongated light sources, wherein each elongated light source is configured to emit ultraviolet light of a short wavelength along a length of the respective elongated light source with an essentially cylindrical symmetrical beam distribution, and wherein each elongated light source extends parallel to a normal of the base area;

a set of rotatable mesh grids rotatably mounted on a frame, wherein the frame surrounds the base area, and the mesh grids are arranged along a perimeter of the base area such that the mesh grids surround the irradiating device, each mesh grid configured to be populated with at least some of the plurality of objects; and a set of reflectors including a set of movable side reflectors, wherein the reflectors are configured to be arranged as to form a resonator surrounding the set of mesh grids surrounding the irradiating device, wherein the set of movable side reflectors include multiple, movable side reflectors configured to provide access to each mesh grid for mounting and dismounting the objects.

\* \* \* \* \*